(12) United States Patent
Goto et al.

(10) Patent No.: US 7,575,585 B2
(45) Date of Patent: *Aug. 18, 2009

(54) INTRAVASCULAR OBSTRUCTION REMOVING WIRE AND MEDICAL INSTRUMENT

(75) Inventors: Katsuya Goto, Fukuoka (JP); Takashi Kaneko, Ashigarakami-gun (JP); Takeshi Kanamaru, Ashigarakami-gun (JP); Masahiro Takeuchi, Kameoka (JP); Keiji Okada, Kameoka (JP)

(73) Assignees: Terumo Kabushiki Kaisha, Shibuya-Ku, Tokyo (JP); Maruho Hatsujyo Kogyo Co., Ltd., Kyoto-Shi, Kyoto (JP)

( * ) Notice: Subject to any disclaimer, the term of this patent is extended or adjusted under 35 U.S.C. 154(b) by 108 days.

This patent is subject to a terminal disclaimer.

(21) Appl. No.: 11/281,358

(22) Filed: Nov. 18, 2005

(65) Prior Publication Data

US 2006/0116702 A1    Jun. 1, 2006

Related U.S. Application Data

(63) Continuation of application No. 10/185,067, filed on Jul. 1, 2002, now Pat. No. 7,041,116.

(30) Foreign Application Priority Data

Jul. 2, 2001    (JP)    ............................. 2001-201331

(51) Int. Cl.
*A61M 29/00*    (2006.01)
*A61B 17/221*    (2006.01)

(52) U.S. Cl. ...................................... 606/200; 606/114

(58) Field of Classification Search ................. 606/200, 606/191, 127, 159, 113, 114, 194, 198, 110, 606/108; 604/105–109; 623/1.11
See application file for complete search history.

(56) References Cited

U.S. PATENT DOCUMENTS 3,435,826 A    4/1969    Fogarty (Continued)

FOREIGN PATENT DOCUMENTS

EP    0 472 368 A2    2/1992

(Continued)

*Primary Examiner*—Anhtuan T. Nguyen
*Assistant Examiner*—Elizabeth Houston
(74) *Attorney, Agent, or Firm*—Buchanan Ingersoll & Rooney PC (57) ABSTRACT

An intravascular obstruction removing wire includes an elongate wire body, at least two non-branched wire portions having distal ends and proximal ends which are connected to a distal end of the wire main body, and a plurality of filament portions extending across the wire portions. The non-branched wire portions and the filament portions form a trapping portion. The trapping portion is deformable from a large-diameter state in which the non-branched portions branch to the distal end of the wire body forward in different directions and the filament portions are separated from each other, so that a space surrounded by the non-branched wire portions and the filament portions is formed to trap therein an obstruction in a blood vessel, to a small-diameter state in which the non-branched wire portions are positioned so that a distance between the wire portions is smaller than that of the wire portions in the large-diameter state.

26 Claims, 7 Drawing Sheets

U.S. PATENT DOCUMENTS

| | | | |
|---|---|---|---|
| 4,590,938 A | 5/1986 | Segura et al. | |
| 4,842,579 A | 6/1989 | Shiber | |
| 4,890,611 A | 1/1990 | Monfort et al. | |
| 5,098,441 A * | 3/1992 | Wechler | 606/113 |
| 5,215,521 A | 6/1993 | Cochran et al. | |
| 5,370,653 A | 12/1994 | Cragg | |
| 5,735,289 A | 4/1998 | Pfeffer et al. | |
| 5,779,716 A * | 7/1998 | Cano et al. | 606/114 |
| 5,895,398 A | 4/1999 | Wensel et al. | |
| 6,093,196 A | 7/2000 | Okada | |
| 6,099,534 A * | 8/2000 | Bates et al. | 606/127 |
| 6,168,603 B1 | 1/2001 | Leslie et al. | |
| 6,224,612 B1 | 5/2001 | Bates et al. | |
| 6,264,663 B1 * | 7/2001 | Cano | 606/114 |
| 6,299,612 B1 * | 10/2001 | Ouchi | 606/47 |
| 6,402,771 B1 * | 6/2002 | Palmer et al. | 606/200 |
| 6,458,145 B1 | 10/2002 | Ravenscroft et al. | |
| 6,520,968 B2 * | 2/2003 | Bates et al. | 606/113 |
| 6,793,666 B2 * | 9/2004 | Hansen et al. | 606/200 |
| 6,918,921 B2 * | 7/2005 | Brady et al. | 606/200 |
| 2002/0068944 A1 | 6/2002 | White et al. | |
| 2003/0120303 A1 * | 6/2003 | Boyle et al. | 606/200 |
| 2003/0144685 A1 * | 7/2003 | Boyle et al. | 606/200 |
| 2004/0006361 A1 | 1/2004 | Boyle et al. | |

FOREIGN PATENT DOCUMENTS

| | | |
|---|---|---|
| EP | 0 791 340 A1 | 8/1997 |
| JP | 5-137729 | 6/1993 |
| JP | 7-171156 | 7/1995 |
| JP | 8-187294 | 7/1996 |
| JP | 2000-126303 | 5/2000 |
| WO | 94/00178 A1 | 1/1994 |
| WO | 95/31149 A1 | 11/1995 |
| WO | 96/23446 A1 | 8/1996 |
| WO | 99/16363 A1 | 4/1999 |
| WO | 01/45569 A1 | 6/2001 |
| WO | 02/43600 A1 | 6/2002 |

* cited by examiner

INTRAVASCULAR OBSTRUCTION REMOVING WIRE AND MEDICAL INSTRUMENT

This application is a continuation of, and claims priority under 35 U.S.C. § 120to, U.S. application Ser No. 10/185,067 filed on Jul. 1, 2002, now U.S. Pat. No. 7,041,116 the entire content of which is incorporated herein by reference.

CROSS-REFERENCE TO RELATED APPLICATIONS

This application is based upon and claims the benefit of priority from the prior Japanese Patent Application No. 2001-201331, filed Jul. 2, 2001, the entire contents of which are incorporated herein by reference.

BACKGROUND OF THE INVENTION

1. Field of the Invention

The present invention relates to an intravascular obstruction removing wire and medical instrument for removing an obstruction, for example, an embolus in a blood vessel.

2. Description of the Related Art

Death cases and sequelae caused by strokes increase in recent years, and postapoplectic therapy needs to be established as soon as possible. As a typical postapoplectic treatment, a thrombolytic treatment using a thrombolytic agent has been developed to treat acute cerebral infarct, and has achieved a satisfactory treatment effect. With the thrombolytic agent, however, sometimes thrombolysis takes time. A thrombus which is reduced in size may be scattered to form another embolus portion. Some thrombus may not be dissolved by the thrombolytic agent. These inconveniences are acknowledged from the clinical experiences of doctors.

In the case of a cerebral infarct, if the blood flow can be resumed within three hours after the infarct is developed, not only the probability of saving the patient's life increases, but also sequelae can be reduced. This is verified in the U.S.A and Europe. Development of a medical instrument that can be inserted in a cerebral blood vessel and can directly remove a thrombus has accordingly been strongly sought for.

Conventionally, as an apparatus for removing a thrombus or obstruction in a blood vessel, for example, a Fogarty catheter of, e.g., U.S. Pat. No. 3,435,826 by Fogarty, an expandable thrombus removing balloon, a water-jet thrombus sucking apparatus, and an atheroma cutter of U.S. Pat. No. 4,842,579 have been made practicable and used. These apparatuses have a complicated structure and a large diameter, and are used alone or require a thick guide catheter. An apparatus that can be inserted in a microcatheter has not been made practicable.

For example, an ablation catheter with a wire basket is typically disclosed in Jpn. Pat. Appln. KOKAI Publication No. 5-137729 (EP 472,368). This catheter has an acute angled portion in part of its wire cage in order to ablate tissue from the inner wall of a blood vessel. The catheter also has a wire guide at its center to support the wire cage. The diameter of this catheter cannot essentially be reduced to be equal or smaller than that of the wire guide. In other words, the wire guide is indispensable for ablating the tissue by rotating the wire cage. Accordingly, the diameter of this catheter cannot be reduced to be equal or smaller than that of the wire guide.

Japanese Patent No. 2,620,881 (U.S. Pat. No. 4,890,611) discloses an endarterectomy apparatus with a wire loop. This apparatus is designed to shear arteriosclerotic deposits. With the structure of this apparatus, it is difficult to hold a thrombus that blocks up a blood vessel. More specifically, a central wire and helical loops cannot form a large holding space, but can merely provide a narrow space where the sheared tissue is to be held. Due to the presence of the central wire, a thrombus cannot be easily accommodated in the helical loops. Therefore, the tissue to be ablated can merely be sandwiched between the central wire and the helical loops.

Jpn. Pat. Appln. KOHYO Publication No. 8-509411 (WO95/31149) discloses a single-loop medical collecting instrument formed of a snare coil. This tool is used to rearrange or extract an obstruction by nipping it with an adjustable-diameter single loop. A medical collecting instrument of the type conventionally called a single-loop gooseneck snare has a simple structure, and its diameter can be reduced. With this instrument, a target obstruction is trapped in the single ring of a single wire, and is held by fastening the ring. Although this instrument is suitable for holding a thin, elongated rod-like obstruction, it is difficult for this instrument to grip an obstruction such as a thrombus which is slippery. In other words, when the target obstruction is a thrombus, to hold it is equivalent to fixing an egg by applying the loop of one wire around it. Although this instrument can be theoretically used, it is difficult to hold an obstruction with the instrument except for a highly-skilled operator.

Jpn. Pat. Appln. KOKAI Publication No. 2000-126303 discloses a multi-functional wire for blood vessel treatment which can be inserted in a microcatheter. This multi-functional wire is of the type conventionally called a basket forceps. A basket which can be contracted and expanded by a wire is formed at the distal end of the wire. This multi-functional wire is obtained by refining a conventional basket forceps by making it much thinner. This multi-functional wire integrally has an expanding action part which is radially dispersed or expanded and gathered or adhered at a convergence point. Hence, in this multi-function wire, the constituent fine lines lose the degree of freedom, and a thrombus cannot be accommodated in the basket easily.

Jpn. Pat. Appln. KOHYO Publication No. 7-504595 (WO94/00178) discloses an instrument in which an expandable metal net is attached to the distal end of a catheter. In this instrument, as the metal net is attached to the distal end of the catheter, it is difficult to reduce the outer diameter of the instrument to be smaller than that of the catheter.

Jpn. Pat. Appln. KOKAI Publication No. 7-171156 (U.S. Pat. No. 5,370,653) proposes an apparatus which removes a thrombus by enmeshing it with a wire brush. Although this apparatus is useful for enmeshing a glue-like soft obstruent such as fibrin, it is difficult for this apparatus to remove a hard thrombus or the like that blocks up a blood vessel. Therefore, when the obstruction is a soft obstruent such as fibrin, it can be removed better by dissolving it with a dissolving agent such as streptokinase or urokinase rather than by removing it by force with this apparatus.

As a technique for removing a hard thrombus that blocks up a blood vessel, a wire disclosed in U.S. Pat. No. 5,895,398 is known. This wire has, at its distal end, a screw structure that can be inserted in a microcatheter. According to this apparatus, the screw portion is screwed into a thrombus like a cork screw. The thrombus is collected just like uncorking a wine bottle. This apparatus is not reliable because, when the screw is screwed into the thrombus, the thrombus may slip off and escape easily. Moreover, the screw may undesirably damage the blood vessel by piercing it.

Jpn. Pat. Appln. KOKOKU Publication No. 4-47574 (U.S. Pat. No. 4,590,938) proposes a wire basket-type medical retriever having a coaxial central sheath. This retriever is characterized in that a large number of wires form a bulbshaped obstruction trapping space. This apparatus must have a shaft sheath at its center. Due to the presence of the shaft sheath, this apparatus cannot provide a large trapping space.

BRIEF SUMMARY OF THE INVENTION

It is an object of the present invention to provide an intravascular obstruction removing wire and medical instrument which can remove an obstruction such as an embolus in a blood vessel by trapping it comparatively reliably with a simple structure.

According to an aspect of the present invention, there is provided an intravascular obstruction removing wire comprising: an elongate wire body with a distal end; at least two non-branched wire portions having distal ends and proximal ends which are connected to the distal end of the wire main body; and a plurality of filament portions extending across the wire portions, wherein the non-branched wire portions and the filament portions form a trapping portion, and the trapping portion is deformable from a large-diameter state in which the non-branched portions branch to the distal end of the wire body forward in different directions and the filament portions are separated from each other, so that a space surrounded by the non-branched wire portions and the filament portions is formed to trap therein an obstruction in a blood vessel, to a small-diameter state in which the non-branched wire portions are positioned so that a distance between the wire portions is smaller than that of the wire portions in the large-diameter state.

According to another aspect of the present invention, there is provided a medical instrument comprising: a catheter having a lumen and a distal end face to be positioned in a blood vessel; and an obstruction removing wire inserted in the lumen and inserted in the blood vessel from the distal end face, the obstruction removing wire comprising an elongate wire body with a distal end, at least two non-branched wire portions with distal ends and proximal ends which are connected to the distal end of the wire main body, and a plurality of filament portions extending across the wire portions, wherein the non-branched wire portions and the filament portions form a trapping portion, and the trapping portion is set in a large-diameter state, when projecting from a front end face of the catheter, in which the non-branched portions branch from the distal end of the wire body forward in different directions and the filament portions are separated from each other, so a space surrounded by the non-branched wire portions and the filament portions is formed to trap therein an obstruction in a blood vessel, and is set in a small-diameter state, when positioned in the lumen of the catheter, in which the non-branched wire portions are regulated by an inner surface of the lumen and the space between the non-branched wire portions becomes narrow.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

An intravascular obstruction removing wire and medical instrument according to the present invention will be described in detail by way of preferred embodiments shown in the accompanying drawings.

First, the first embodiment will be described with reference to FIGS. 1 to 3D. In the following description, the upper side and lower side are respectively called "the proximal end" and "distal end" in FIGS. 1 and 2. The right side and left side are respectively called "the proximal end" and "distal end" in FIGS. 3A to 3D. Generally, the proximal end side of the wire is maintained outside the human body, and the distal end thereof is inserted in a blood vessel of the human body.

An intravascular obstruction removing wire 1A shown in FIGS. 1 and 2 serves to trap and remove an obstruction (to be referred to as "embolus" hereinafter) such as a thrombus or clot in the blood vessel, that causes embolism.

The intravascular obstruction removing wire 1A has an elongate wire body 2 and a trapping portion 3. The trapping portion 3 is formed or provided at the distal end of the wire body 2 and can trap an embolus in the blood vessel. The wire body 2 has appropriate rigidity and elasticity (flexibility) over its entire length. The structure of the wire body 2 is not particularly limited. For example, the wire body 2 can be a solid single wire, a hollow single wire, a bundle of a plurality of solid or hollow single wires, or a multilayered-structure wire. Alternatively, a single wire or a plurality of wires may be used as a core, and a coil may be wound on the core, thus forming the wire body 2. Alternatively, these structures may be appropriately combined to form the wire body 2. The material of the wire body 2 is not particularly limited. Various types of metal materials, plastics or the like may be used alone or in combination to form the wire body 2.

As the wire body 2, a commercially available (existing) guide wire (a wire used to guide a catheter or the like to a target portion in the living body) or a known guide wire can be employed. For example, a plastic type guide wire (e.g., tradename "Radifocus Guide Wire" manufactured by TERUMO CORP.) using a superelastic-alloy taper wire as the core wire, or a guide wire having a superelastic far-end described in Jpn. Pat. Appln. KOHYO Publication No. 9-508538 can be suitably used.

The preferable length of the wire body 2 changes depending on the cases, e.g., the position or size of the blood vessel to which the wire body 2 is to be applied. Usually, a length of about 500 mm to 4,000 mm is preferable, and a length of 1,500 mm to 2,200 mm is more preferable.

The wire body 2 need not have the same characteristics over its entire length. Preferably, the wire body 2 is formed such that its rigidity (bending rigidity, torsional rigidity, or the like) decreases continuously or intermittently, that is, it becomes flexible, from its proximal end toward its distal end. As an example, the wire body 2 preferably has a first portion, a third portion, and at least one second portion. The first portion is located on the proximal end side and is comparatively hard. The third portion is located at the distal end side and is comparatively flexible. The second portion is located between the first and third portions and has an intermediate hardness between them. When a wire body with a specific rigidity is used in this manner, operation at the operator's hand is reliably transmitted to the distal end. Then, the wire body 2 travels well in the blood vessel and can be operated well at a corner. Also, the flexibility at the distal end of the wire body 2 is improved, so any damage to the blood vessel may be prevented. In other words, a higher safety can be ensured while maintaining the torque transmitting properties, push-in properties (pushability), and kink resistance (bending resistance) of the wire body 2.

The preferable diameter (thickness) of the wire body 2 changes depending on the cases, e.g., the position or size of the blood vessel to which the wire body 2 is to be applied. Usually, an average diameter of 0.1 mm to 2.0 mm is preferable, and an average diameter of 0.25 mm to 0.9 mm is more preferable.

In particular, with the intravascular obstruction removing wire 1A which is used upon insertion in a microcatheter, the average diameter of the wire body 2 is preferably about 0.1 mm to 0.53 mm (0.004 inch to 0.021 inch), and is more preferably about 0.25 mm to 0.46 mm (0.010 inch to 0.018 inch).

A microcatheter is an intravascular treating/analytic catheter with an outer diameter of less than 4 Fr. (French), and is clearly identified from an angiographic catheter, guiding catheter, or the like with an outer diameter of 4 Fr (about 1.33 mm) or more.

The present invention is not limited to an intravascular obstruction removing wire suitable for a microcatheter. It will be readily understood that the present invention can similarly be applied to an intravascular obstruction removing wire used for obstruction collection in a large blood vessel, which is suitable for, e.g., an angiographic catheter or guiding catheter.

Figure 3A:
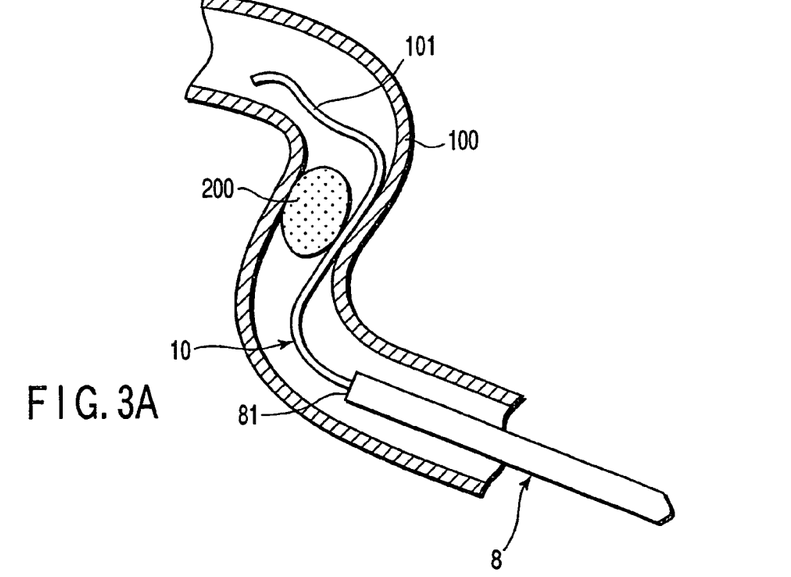
FIGS. 3A to 3D are views for sequentially explaining how to use the intravascular obstruction removing wire shown in FIGS. 1 and 2.

The wire body 2 may be a combination of a wire and a covering layer. The covering layer covers the outer surface (surface) of the wire to reduce the frictional resistance with the inner surface of a catheter 8 (FIG. 3A). Then, the wire body 2 can be inserted in and extracted from the catheter 8 more smoothly. For example, the covering layer may be a covering layer (Teflon coating) made of a fluoroplastic such as polytetrafluoroethylene, or hydrophilic coating which exhibits wetting properties when it is wet.

The trapping portion 3 is attached to the distal end of the wire body 2 to extend forward. In a natural state, the width of the trapping portion 3 is enlarged (opened) (this state will be referred to as a "large-diameter state" hereinafter), as shown in FIGS. 1 and 2. In the large-diameter state, the trapping portion 3 forms a shape with a space (recess) 31 where an embolus 200 (FIG. 3A) in a blood vessel 100 can be trapped.

The trapping portion 3 can be deformed from the large-diameter state to be folded in the radial direction (widthwise direction) so it is contracted to such a size (width) that it can be accommodated in the lumen of the catheter 8 (this state will be referred to as a "small-diameter state" hereinafter). In the small-diameter state, non-branched wire portions 4a and 4b are bound by the inner surface of the lumen of the catheter 8, so that the space between the portions 4a, 4b is narrow. Preferably, the trapping portion 3 is deformable so when it is extracted from the catheter, it is naturally restored from the small-diameter state to the large-diameter state by its own elastic restoring force.

In the following description, an explanation on the shape and size of the trapping portion 3 refers to those in the large-diameter state unless otherwise specified.

The trapping portion 3 is formed of the two non-branched wire portions 4a and 4b, and a plurality of filament portions 5. The wire portions 4a and 4b forwardly extend from the distal end of the wire body 2 so as to branch (to separate from each other) in one plane in directions to separate from each other. The filament portions 5 extend across the wire portions 4a and 4b with both ends connected to the wire portions. In the present invention, the term "non-branched wire portions" refer to wire portions which do not branch halfway therein.

The proximal ends of the non-branched wire portions 4a and 4b are fixed to the distal end of the wire body 2. The fixing method is not particularly limited. For example, the proximal ends of the non-branched wire portions 4a and 4b may be knitted (wound), welded by brazing or the like, or adhered with an adhesive to the distal end of the wire body 2, thereby fixing them. In this embodiment, a coil 21 is wound around the distal end of the wire body 2. The coil 21 covers the fixing portions (brazing portions) of the non-branched wire portions 4a and 4b with respect to the wire body 2. The outer surface of the coil 21 is smooth, so a high safety is obtained. The coil 21 is preferably formed by winding a platinum wire or tape, or the like.

Figure 1:
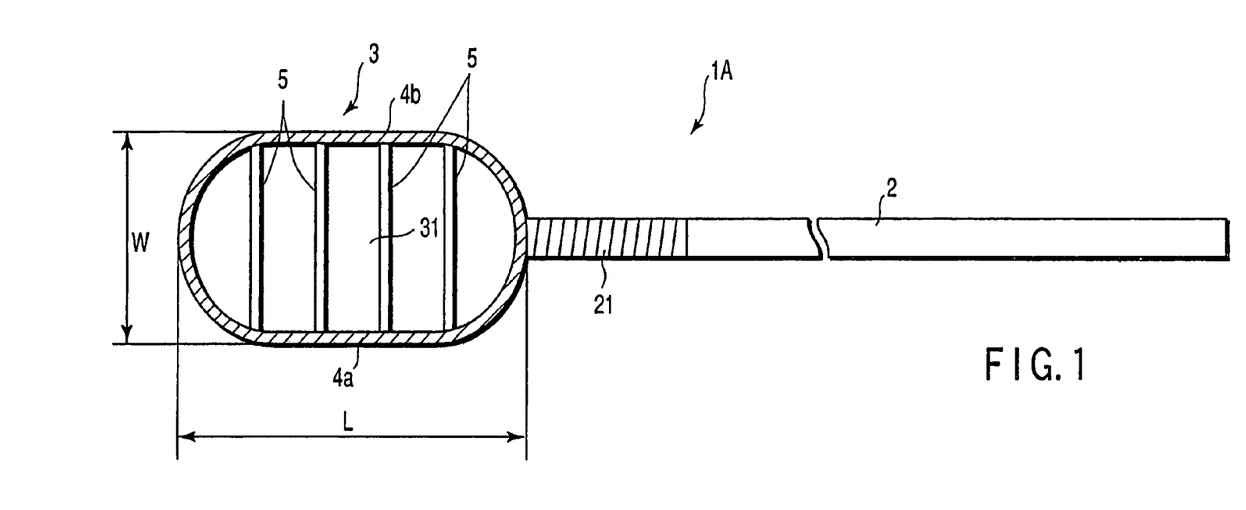
FIG. 1 is a plan view showing an intravascular obstruction removing wire according to the first embodiment of the present invention.
Figure 2:
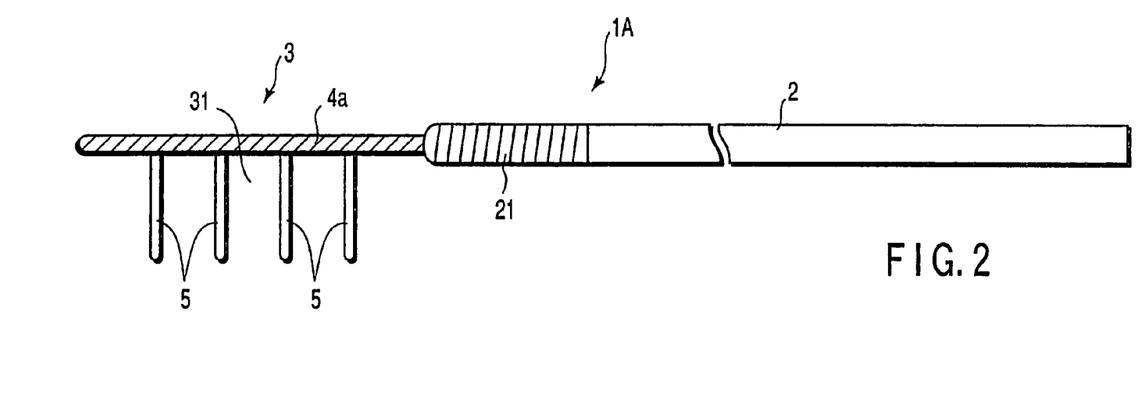
FIG. 2 is a side view showing the obstruction removing wire shown in FIG. 1.

As shown in FIG. 1, the distal ends of the non-branched wire portions 4a and 4b are connected to each other. More specifically, the distal end of the non-branched wire portion 4a continues to that of the non-branched wire portion 4b. In this embodiment, both non-branched wire portions 4a and 4b are integrally formed of one wire. Hence, the non-branched wire portions 4a and 4b form a loop (ring) as a whole. When the embolus 200 is trapped, the distal ends of the non-branched wire portions 4a and 4b cover it from the distal end side. Thus, the embolus 200 can be held more reliably.

The filament portions 5 between the non-branched wire portions 4a and 4b are formed of a plurality of (four in this embodiment) linear thin wires, and extend across the non-branched wire portions 4a and 4b. The filament portions 5 preferably extend parallel to each other, but the present invention is not limited to this. The filament portions 5 are curved with respect to the non-branched wire portions 4a and 4b so they suspend (hang) to the lower side in FIG. 2. In other words, the filament portions 5 suspend in a curved manner between the wire portions 4a and 4b.

As the wire portions 4a and 4b and the filament portions 5 are arranged in this manner, the space (recess) 31 which is defined between them to trap the embolus 200 is formed in the trapping portion 3.

The intravascular obstruction removing wire 1A traps the embolus 200 in this space 31. Hence, the embolus 200 which is trapped once will not drop (separate), so the embolus 200 can be removed reliably.

The number of filament portions 5 is not particularly limited, but is preferably 2 to 20, and is more preferably 2 to 6.

In this embodiment, each of the non-branched wire portions 4a and 4b is formed of a strand obtained by twisting a plurality of (preferably approximately two to six) wires (linear bodies). The fixing portions (two ends) of each filament portion 5 with respect to the wire portions 4a and 4b are fixed as they are sandwiched (twisted) in the strands that form the wire portions 4a and 4b. With this arrangement, the filament portions 5 can be fixed to the wire portions 4a and 4b easily and firmly.

According to the present invention, the size of the trapping portion 3 can be set freely. The preferable size of the trapping portion 3 differs depending on the diameter, etc. of the blood vessel into which the intravascular obstruction removing wire is to be applied. Usually, the size of the trapping portion 3 is as follows. An entire length L of the trapping portion 3 in FIG. 1 is preferably 2 mm to 40 mm, and is more preferably 4 mm to 20 mm. An outer diameter (width) W of the trapping portion 3 in FIG. 1 is preferably 1 mm to 30 mm, and is more preferably 2 mm to 10 mm. Consequently, the space 31 preferably has a width of 2 mm to 10 mm, a length of 4 mm to 20 mm, and a depth of 1 mm to 5 mm.

In particular, when the intravascular obstruction removing wire is to be used for a middle cerebral artery terminal portion (M1 portion) where cerebral infarct often occurs, the trapping portion 3 preferably has an entire length (the length L in FIG. 1) of about 5 mm to 10 mm and an outer diameter (the length W in FIG. 1) of about 3 mm to 5 mm. This is due to the following reason. At the deutocerebrum artery terminal portion, the inner diameter of the blood vessel is about 4 mm. It is acknowledged from the clinical experiences of doctors. That many of the thrombi that cause embolism have a diameter of about 4 mm and a length of about 7 mm.

As described above, the trapping portion 3 can be deformable to a small-diameter state so it can be inserted into the lumen (inner cavity) of the catheter 8. According to this embodiment, the trapping portion 3 has a comparatively simple structure as described above. This is advantageous in reducing the diameter of the trapping portion 3 in the small-diameter state.

In particular, in this embodiment, when the trapping portion 3 comes out from the lumen of the catheter 8, the comparatively large-rigidity (comparatively thick) non-branched wire portions 4a and 4b reliably cause the trapping portion 3 to be automatically restored to the large-diameter state by its restoring force. Thus, the embolus can be accommodated in the space 31. After that, the wire body 2 is pulled with respect to the catheter 8, so the trapping portion 3 gradually enters the lumen from its proximal end side. Consequently, the trapping portion 3 is gradually contracted in diameter, so the entire non-branched wire portions 4a and 4b fasten and sandwich the embolus 200. In addition, the comparatively flexible (comparatively thin) filament portions 5 hold the thrombus 200 to support it from below so as to prevent it from dropping.

Hence, the trapping portion 3 can achieve both the reliability to trap the embolus 200 and the diameter-reducing properties in the small-diameter state.

Since the trapping portion 3 can be reduced in diameter to almost the same size as that of an ordinary guide wire, the intravascular obstruction removing wire 1A can be used in combination with the existing microcatheter.

In general, the value of a ratio W/W' of the outer diameter (W) of the trapping portion 3 in the large-diameter state to an outer diameter (width) W' thereof in the small-diameter state is preferably about 1.1 to 20, and is more preferably about 1.1 to 10. In particular, when the intravascular obstruction removing wire is of a type which is used upon insertion in a microcatheter, the outer diameter W' in the small-diameter state is preferably 0.53 mm (0.021 inch) or less, and is more preferably 0.46 mm (0.018 inch) or less.

The materials of the trapping portion 3 (the materials of the wire portions 4a and 4b and filament portions 5) are preferably various types of metal materials. For example, an alloy with spring properties, e.g., stainless steel (SUS304 or the like), β titanium steel, a Co—Cr alloy, a music wire, a platinum-iridium alloy, or a nickel-titanium alloy, can be used.

Among the above metal materials, an alloy which exhibits superelasticity in the living body is particularly preferable as the material of the trapping portion 3. With this material, deformation (displacement) of the trapping portion 3 from the small-diameter state to the large-diameter state can be caused more reliably. Also, a more accurate restored shape of the trapping portion 3 can be obtained in the large-diameter state. An alloy which exhibits superelasticity in the living body is an alloy with the following nature. Namely, when this alloy is deformed (bend, pulled, or compressed) at least at a human body temperature (near 37° C) to a region where an ordinary metal causes plastic deformation, it is restored almost to the original shape. Such an alloy is called a shape memory alloy or superelastic alloy. The type of shape memory alloy or superelastic alloy is not particularly limited, but a titanium-based alloy (Ti—Ni, Ti—Pd, or Ti—Nb—Sn) or a copper-based alloy is preferable. Regarding the preferable composition of such an alloy, for example, the alloy may contain about 30 atm % to 52 atm % of titanium, a balance of nickel, and 10 atm % or less of at least one additional alloy element. The additional alloy element is not particularly limited, but can be selected from a group consisting of, e.g., 3 atm % or less of iron, cobalt, platinum, palladium, or chromium, and 10 atm % or less of copper or vanadium. As the superelastic alloy, one which exhibits an austenite phase at a room temperature or human body temperature (near 37° C.) and is transformed to a martensite phase upon reception of a stress (one which exhibits stress-induced austenite-martensite phase transformation in the vicinity of the human body temperature) is particularly preferable.

The material used for the filament portions 5 is preferably a very thin wire made of a precious metal spring alloy, a nickel-titanium superelastic alloy, or a platinum alloy called Ptlr10, among the materials described above. This is because with this material, the diameters of the filament portions 5 can be reduced and X-ray contrast enhancement can be obtained. Other than these, as the material to form the filament portions 5, a monofilament or multifilament made of a resin, or a platinum alloy wire can be used. The non-branched wire portions 4a and 4b and the filament portions 5 can be made of same material or different materials.

The diameter of the non-branched wire portions 4a and 4b is not particularly limited, but is preferably 0.05 mm to 0.9 mm, and is more preferably 0.3 mm to 0.5 mm. The diameter of the wire portions 4a and 4b refers to the entire outer diameter regarding the strand portion.

The diameter of the filament portions 5 is not particularly limited, but is preferably 0.025 mm to 0.2 mm, and is more preferably 0.05 mm to 0.1 mm.

The surface of the trapping portion 3 (at least that surface portion which is to come into contact with the embolus) may be provided with a non-slip means. Then, the trapped embolus 200 can be held more reliably. As the non-slip means, an elastic material, e.g., rubber, with a comparatively high coefficient of friction, or small recesses and projections (including a rough surface) may be formed by, e.g., sandblasting.

The medical instrument of this embodiment has this intravascular obstruction removing wire 1A (denoted by reference numerals 1B to 1D in embodiments to be described later) and the catheter 8.

An example of how to use the intravascular obstruction removing wire 1A of the present invention will be described in detail with reference to FIGS. 3A to 3D.

FIG. 3A shows a state wherein the blood vessel 100 clogs with the embolus 200 such as a thrombus to block the blood flow. The embolus 200 is urged against the inner wall of the blood vessel 100 by the blood pressure, so it does not move easily.

The catheter (microcatheter) 8 and a guide wire 10 inserted in the lumen of the catheter 8 are inserted in the blood vessel 100, and a distal end opening 81 of the catheter 8 is positioned immediately before the embolus 200. In this state, the guide wire 10 is moved forward with respect to the catheter 8 so that a distal end 101 of the guide wire 10 projecting from the distal end opening 81 is inserted to be deeper (peripheral side) than the embolus 200. More specifically, as shown in FIG. 3A, the distal end 101 of the guide wire 10 is moved to pass through the interval between the embolus 200 and the inner wall of the blood vessel 100 to ride over the embolus 200. This operation can be performed easily by using, as the guide wire 10, a microguide wire with good lubricating properties.

Figure 3B:
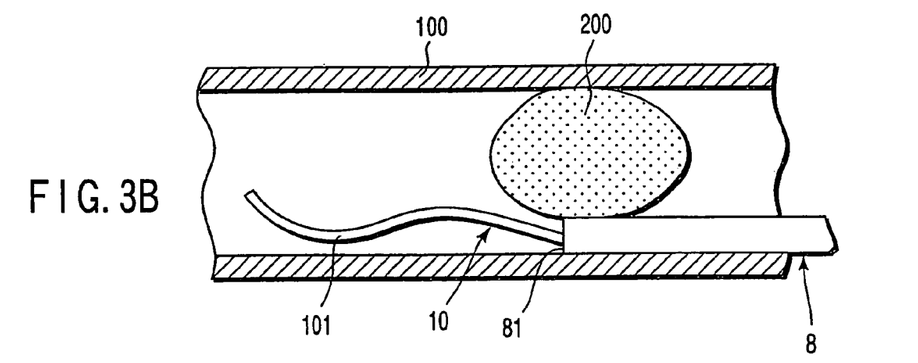

In this state, forward movement of the guide wire 10 is stopped, and the catheter 8 is moved forward with respect to the guide wire 10, i.e., by being guided by the guide wire 10, until the distal end of the catheter 8 enters the interval between the embolus 200 and the inner wall of the blood vessel 100, as shown in FIG. 3B. At this time, the distal end of the catheter 8 smoothly enters the interval along the guide wire 10. Hence, this operation can be performed easily.

According to conventional treatment, a thrombolytic agent is supplied in this state through the catheter 8 in the reverse direction to enhance thrombolysis. Some thrombus, however, cannot be dissolved by the thrombolytic agent, and sometimes thrombolysis takes a long period of time. This is often experienced by doctors. The present invention is useful in such cases as well.

Figure 3C:
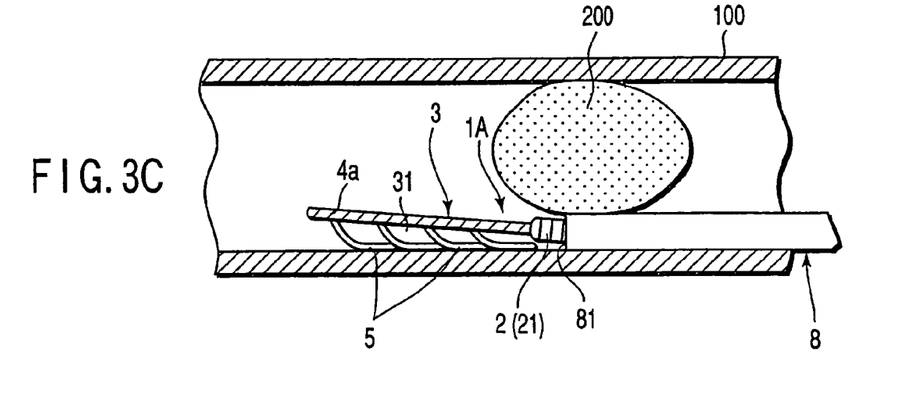

With the catheter 8 being fixed, the guide wire 10 is moved backward with respect to the catheter 8, and is extracted from the lumen of the catheter 8. The intravascular obstruction removing wire 1A with the above arrangement is inserted in the lumen from which the guide wire 10 has been extracted. As shown in FIG. 3C, the trapping portion 3 is caused to project from the distal end opening 81 of the catheter 8. At this time, the trapping portion 3 which has been in the small-diameter state in the catheter 8 develops automatically by its own elasticity so as to be in the large-diameter state. Thus, the space 31 for trapping the embolus 200 is formed.

Subsequently, the catheter 8 and intravascular obstruction removing wire 1A are slightly moved toward the proximal end (direction indicated by an arrow in FIG. 3D). The distal end of the catheter 8 is pulled to the front of the embolus 200.

Figure 3D:
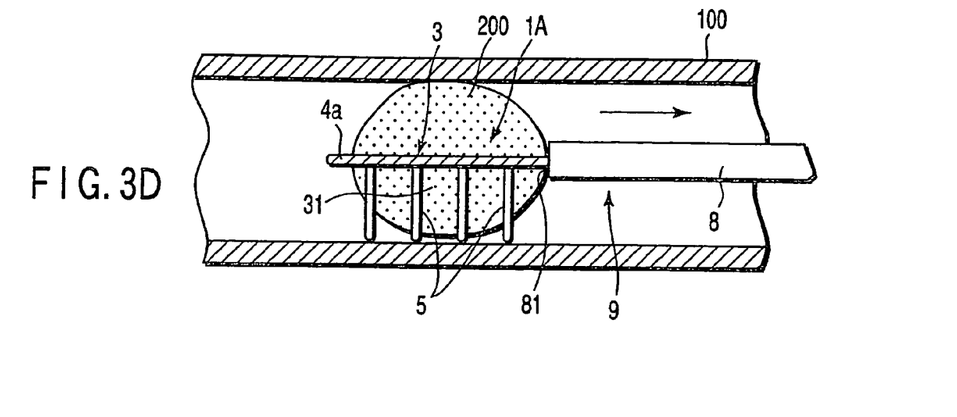

As shown in FIG. 3D, the embolus 200 is picked up in the space 31 of the trapping portion 3 and is trapped (accommodated) in it.

In this state, the wire body 2 is drawn toward the proximal end with respect to the catheter 8. Then, the proximal ends of the non-branched wire portions 4a and 4b come into contact with (the edge of) the distal end opening 81 and are drawn into the catheter 8 while narrowing the interval between them. Thus, the loop formed by the wire portions 4a and 4b becomes small. Consequently, the embolus 200 is fastened by the non-branched wire portions 4a and 4b from its circumference.

This fastening force can break a soft thrombus such as fibrin, thereby solving blocking of the blood vessel 100. An embolus 200 which is not broken is held more reliably by the trapping portion 3 with this fastening force. In this state, the obstruction removing wire 1A is moved backward together with the catheter 8, and is extracted from the patient's body. The embolus 200 which is removed and trapped by the trapping portion 3 of the obstruction removing wire 1A can be collected (removed) in the main guiding catheter or sheath introducer (not shown) in a known manner. When the obstruction removing wire 1A is moved backward, the embolus 200 trapped by the trapping portion 3 is fastened at its side surface by the wire portions 4a and 4b and is supported at its lower surface by the filament portions 5. Thus, the embolus 200 can be collected reliably while it is prevented from dropping (separating) from the trapping portion 3.

In the above operation, the embolus 200 need not always be fastened at its side surface by the non-branched wire portions 4a and 4b. As shown in FIG. 3D, after the embolus 200 is picked up in the space 31 of the trapping portion 3, the wire body 2 may not be drawn toward the proximal end with respect to the catheter 8, but both the catheter 8 and wire body 2 may be moved backward, so they are extracted from the patient's body.

Figure 4:
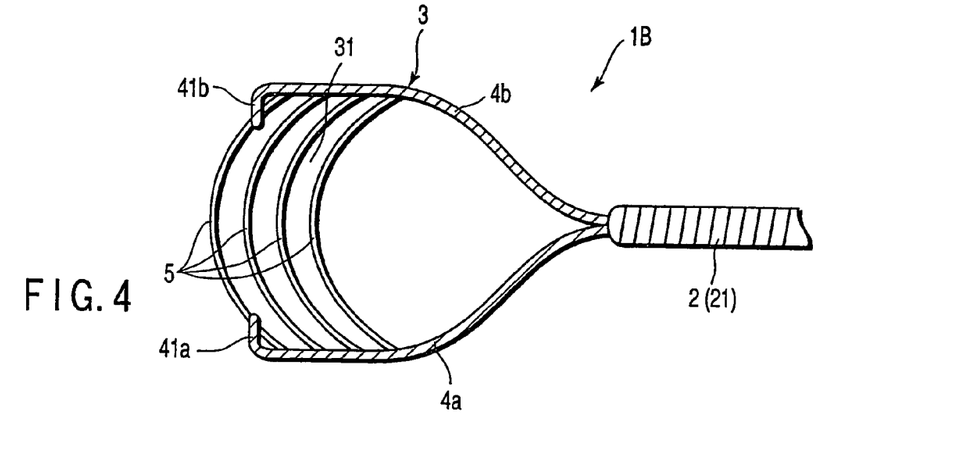
FIG. 4 is a plan view showing the trapping portion of an intravascular obstruction removing wire according to the second embodiment of the present invention.
Figure 5:
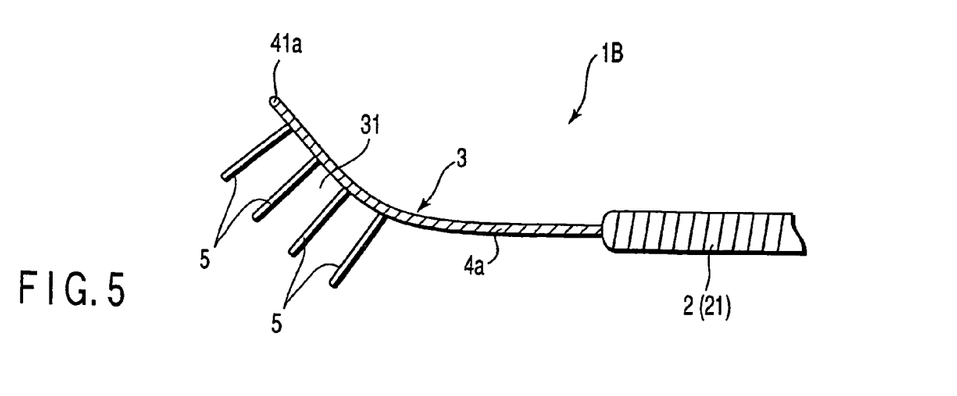
FIG. 5 is a side view showing the trapping portion of the obstruction removing wire shown in FIG. 4.
Figure 6:
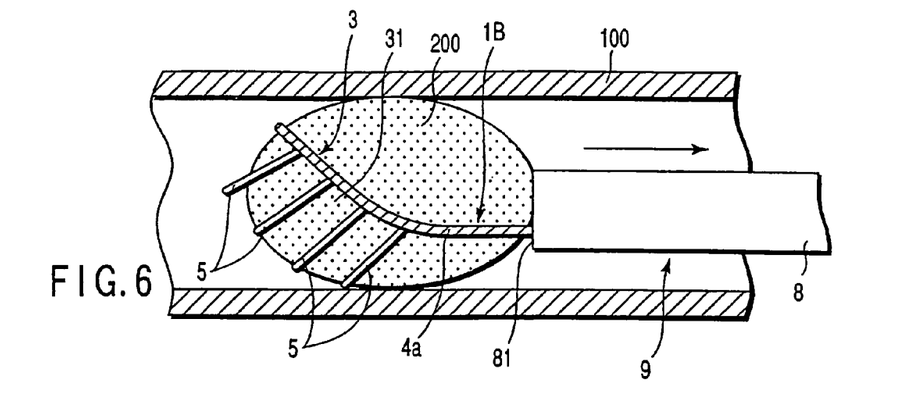
FIG. 6 is a view showing a state wherein an embolus is trapped with the intravascular obstruction removing wire shown in FIGS. 4 and 5.

An intravascular obstruction removing wire according to the second embodiment of the present invention will be described with reference to FIGS. 4 to 6. In FIGS. 4 to 6 and drawing to be described later, components substantially identical or similar to those described in the first embodiment are denoted by the same reference numerals as in the first embodiment, and a detailed description thereof will be omitted.

An intravascular obstruction removing wire 1B according to this embodiment is identical to that of the first embodiment except that the shape of its trapping portion 3 is different.

As shown in FIG. 4, in the trapping portion 3, non-branched wire portions 4a and 4b are formed independently of each other. More specifically, the distal ends of the wire portions 4a and 4b are not connected to each other. The two wire portions 4a and 4b are not positioned on one plane, unlike in the first embodiment, but their distal end portions are bent upward, i.e., in one direction, as clearly seen in FIG. 5. Filament portions 5 connected between the non-branched wire portions 4a and 4b are curved to hang in the opposite direction to the angled direction of the wire portions 4a and 4b, as shown in FIG. 5.

With the intravascular obstruction removing wire 1B having this arrangement, as shown in FIG. 6, when an embolus 200 is trapped by the trapping portion 3, the filament portions 5 support the embolus 200 from below. When the wire body is slightly moved backward with respect to the catheter to fasten the embolus 200, the filament portions 5 fasten the embolus 200 from the distal end side. As a result, when, e.g., the intravascular obstruction removing wire 1B is to be extracted from a blood vessel 100, the embolus 200 which has been trapped once can be prevented more reliably from dropping (separating). It can be understood that, of the filament portions 5, those located at the front portion can be so designed that they can fasten the embolus 200 from its front surface, in the same manner as the wire portions 4a and 4b.

According to this embodiment, the non-branched wire portions 4a and 4b are curved, and their distal ends are separate from each other. This can prevent the distal ends of the wire portions 4a and 4b from damaging the inner wall of the blood vessel 100. This effect is enhanced as distal ends 41a and 41b of the wire portions 4a and 4b are angled inwards.

According to the description of the first and second embodiments, the wire portions 4a and 4b cooperate with a front end face 81 of the catheter 8 to fasten the embolus 200 from the front and behind. The space between the wire portions 4a and 4b becomes narrow as the trapping portion 3 is retracted into the opening 81 of the catheter 8. Hence, it can be understood that the shape of the trapping portion 3 can be designed as required such that the two wire portions 4a and 4b fasten the embolus 200 from the side portions.

An intravascular obstruction removing wire according to the third embodiment of the present invention will be described with reference to FIGS. 7 to 10.

An intravascular obstruction removing wire 1C according to this embodiment is substantially identical to that of the first embodiment except that the shape of its trapping portion 3 is different.

Figure 9:
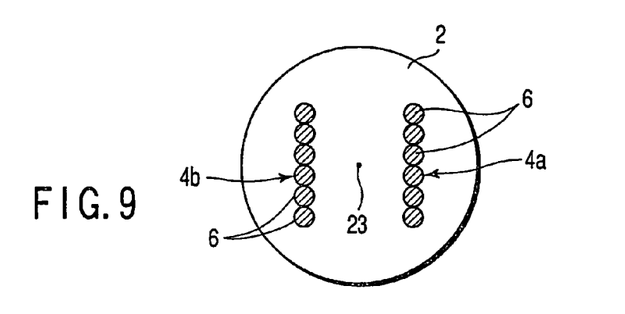
FIG. 9 is a cross-sectional view taken along the line IX-IX of FIG. 8.

In the trapping portion 3, non-branched wire portions 4a and 4b and filament portions 5 are formed of a plurality of (six in this embodiment) loop wires 6 having loop portions of almost the same sizes which are formed at the distal end of a wire body 2 to form loops (rings). The proximal ends of the loop wires 6 are overlaid vertically, i.e., in one direction, as best shown in FIG. 9. As the proximal ends of the respective loop wires 6 enter a catheter 8, they are gradually displaced in an inner direction to narrow the interval between them. Thus, forces that fasten an embolus 200 inwardly act, so the embolus 200 can be gripped between the opposite side portions of each loop wire, and trapped (held) more reliably.

The proximal end portions on one side of the plurality of loop wires 6 each having separate end portions are gathered integrally to form a length of the non-branched wire portion 4a. The proximal end on the other side of the loop wires 6 are also gathered integrally to form a length of the non-branched wire portion 4b. These proximal ends may or may not be adhered to each other with, e.g., an adhesive. Hence, as shown in FIG. 9, the wire portions 4a and 4b are arranged to oppose each other to sandwich a central axis 23 of the wire body 2. This can minimize a thickness t of the proximal ends of the loop wires 6 as a whole shown in FIG. 8, i.e., of the wire portions 4a and 4b. Then, the size of the trapping portion 3 becomes very compact. This is advantageous in reducing the diameter in the small-diameter state. It is preferable that the two proximal end portions of each of the loop wires 6 are brought into tight contact with each other and are aligned integrally, as shown in FIG. 9. However, the present invention need not be limited to this. The portion of the loop wire 6 except for its proximal end constitutes a filament portion. The filament portion 5 includes two connecting portions or ends 5a, 5b respectively connected to the distal ends of said non-branched wire portions 4a and 4b, and a projecting portion or loop section 5c forwardly extending and connected between the connecting ends.

The non-branch wire portions 4a and 4b have a length l and/or distance L1 that depends on the diameter and the like of the blood vessel to which the trapping portion is applied. Usually, the wire portions 4a and 4b extends in the axis for the distance L1 that is preferably about 20 to 80%, more preferably about 30 to 70% of the overall length L of the trapping portion 3. If the trapping portion to be applied to the middle cerebral terminal portion, the wire portions 4a and 4b have the length l of preferably about 3 to 12 mm, more preferably 5 to 8 mm.

In this embodiment, the non-branched wire portions 4a and 4b extend in the same plane. This renders the trapping portion 3 very compact. Hence, the trapping portion 3 can have a small diameter in its small-diameter state.

Figure 8:
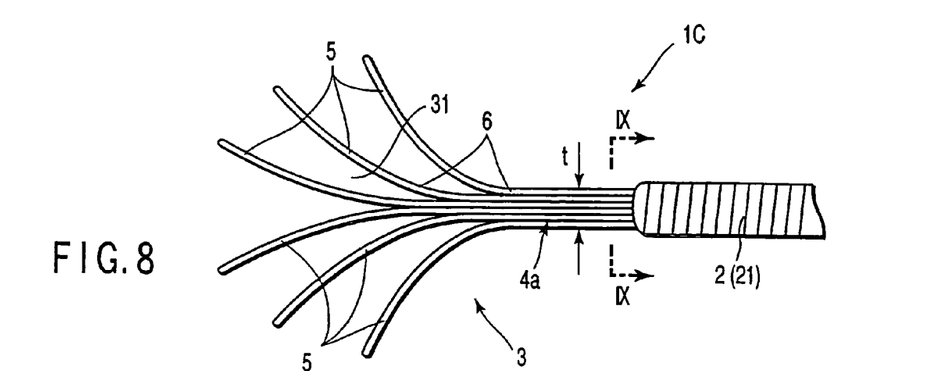
FIG. 8 is a side view showing the trapping portion of the obstruction removing wire shown in FIG. 7.

As shown in FIG. 8, the loop wires 6 are angled or curved (the term "angled" means to be bent linearly to form a predetermined angle, and the term "curved" means to be bent with a curvature, both of which will be described as being "turned" hereinafter) halfway (at portions adjacent to the proximal ends) outwardly (in the vertical direction in FIG. 8) at predetermined angles with respect to a plane where the non-branched wire portions 4a and 4b extend. In the plurality of loop wires 6, those portions extending from their turned portions to the distal end side are separate from each other to form filament portions 5. The angle of turning (radius of curvature) differs among the loop wires 6. In the arrangement shown in FIG. 8, the outer loop wires 6 are turned at larger angles (the radii of curvature of the outer loop wires 6 are smaller). With this arrangement, the trapping portion 3 as a whole has a basket-like shape in which the intervals between the adjacent loop wires 6 increase toward the distal ends of the loop wires 6. When the loop wires 6 are angled, they may be angled at a plurality of portions. In this case, the angles of angling are preferably set to increase toward the distal ends of the loop wires 6. It suffices as far as at least some of the plurality of loop wires 6 are halfway turned outwardly. For example, only the outer loop wires 6 may be turned, while the loop wire 6 (at the center) sandwiched by the outer loop wires 6 may not be turned. Preferably, when an odd number of loop wires are to be used, the loop wire at the center is not turned, while the same numbers of turned looped wires are disposed on the two sides of the loop wire at the center to sandwich it. When an even number of loop wires are to be used, no turned loop wire is provided at the center.

Figure 7:
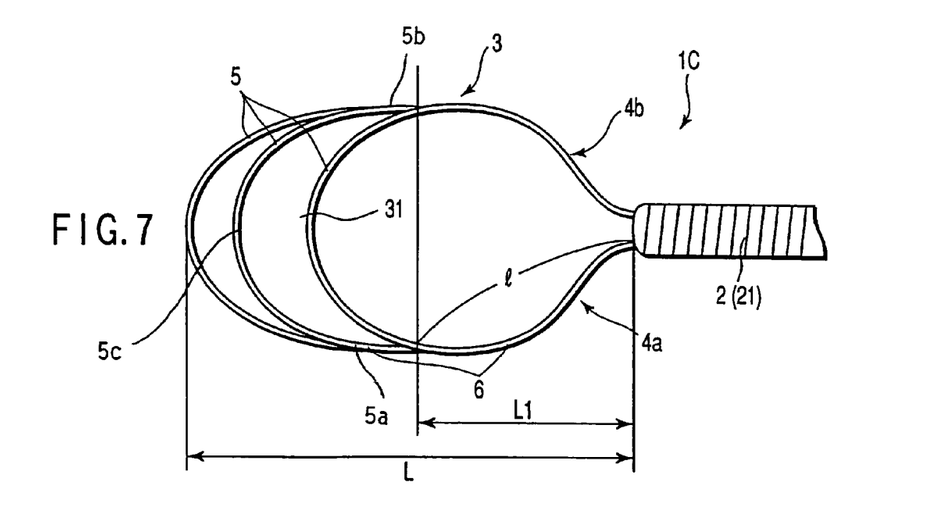
FIG. 7 is a plan view showing the trapping portion of an intravascular obstruction removing wire according to the third embodiment of the present invention.

As shown in FIG. 7, the distal ends of the filament portions 5 are smoothly curved. This can prevent damage to the inner wall of a blood vessel 100, thus providing a higher safety.

In this embodiment, the number of loop wires 6 is not particularly limited, but is preferably 2 to 20, and is more preferably 4 to 10. The diameter (average diameter) of the loop wires 6 is not particularly limited, but is preferably 0.025 mm to 0.2 mm, and is more preferably 0.05 mm to 0.1 mm.

Figure 10:
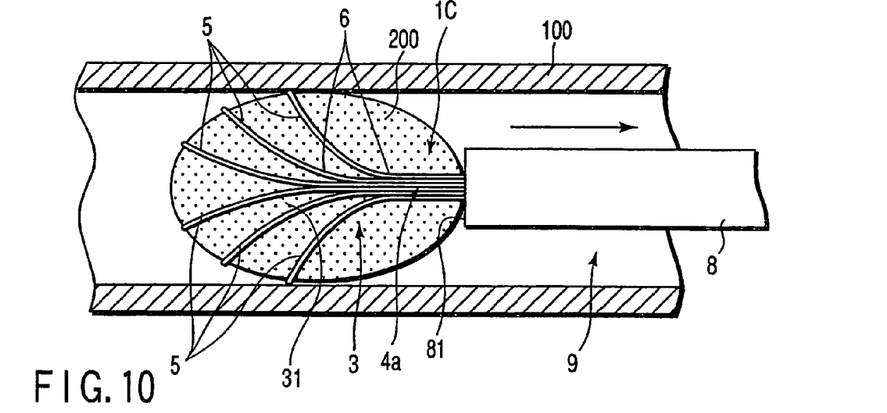
FIG. 10 is a view showing a state wherein an embolus is trapped with the intravascular obstruction removing wire shown in FIGS. 7 to 9.

As shown in FIG. 10, with the intravascular obstruction removing wire 1C having the above arrangement, an embolus 200 is caught in a space 31 surrounded by the loop portions of the loop wires 6. The wire body 2 is drawn toward the proximal end with respect to the catheter 8, as indicated by an arrow. Then, the embolus 200 can be sandwiched among the filament portions 5, the non-branched wire portions 4a and 4b, and the end face of the catheter 8. As a result, the embolus 200 can be reliably trapped by the trapping portion 3. After this, the catheter 8 and obstruction removing wire 1C are operated in the same manner as in the above embodiments, to remove the embolus 200 from the patient's body.

The fourth embodiment of the present invention will be described with reference to FIGS. 11 to 13.

Figure 11:
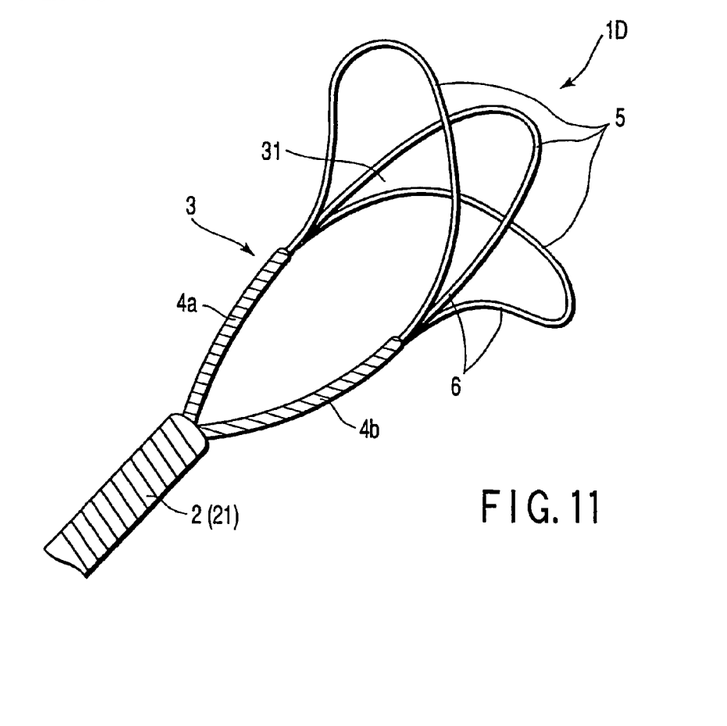
FIG. 11 is a perspective view showing the trapping portion of an intravascular obstruction removing wire according to the fourth embodiment of the present invention.
Figure 12:
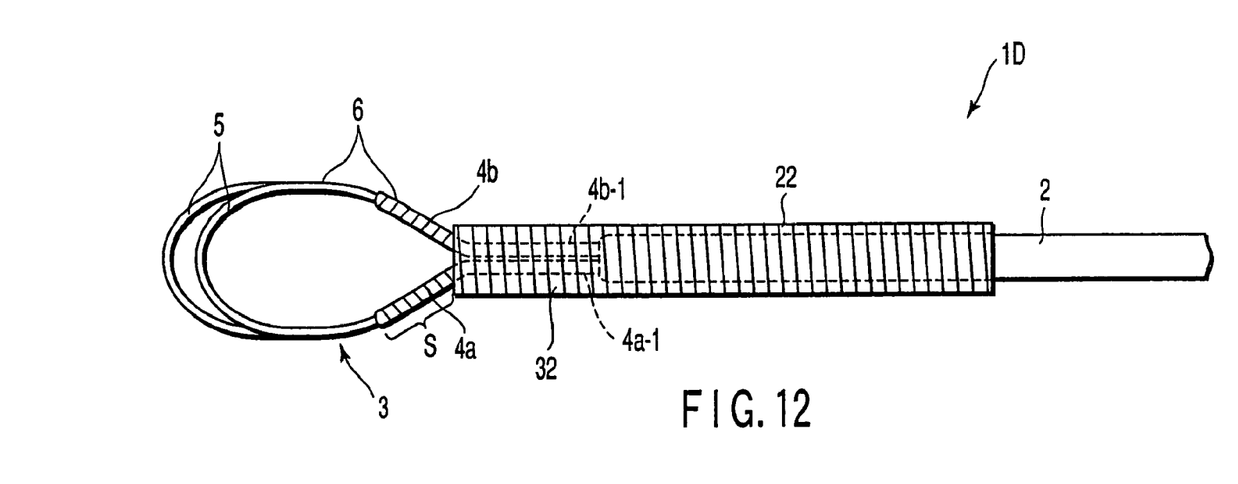
FIG. 12 is a plan view showing the entire portion of the intravascular obstruction removing wire according to the fourth embodiment.
Figure 13:
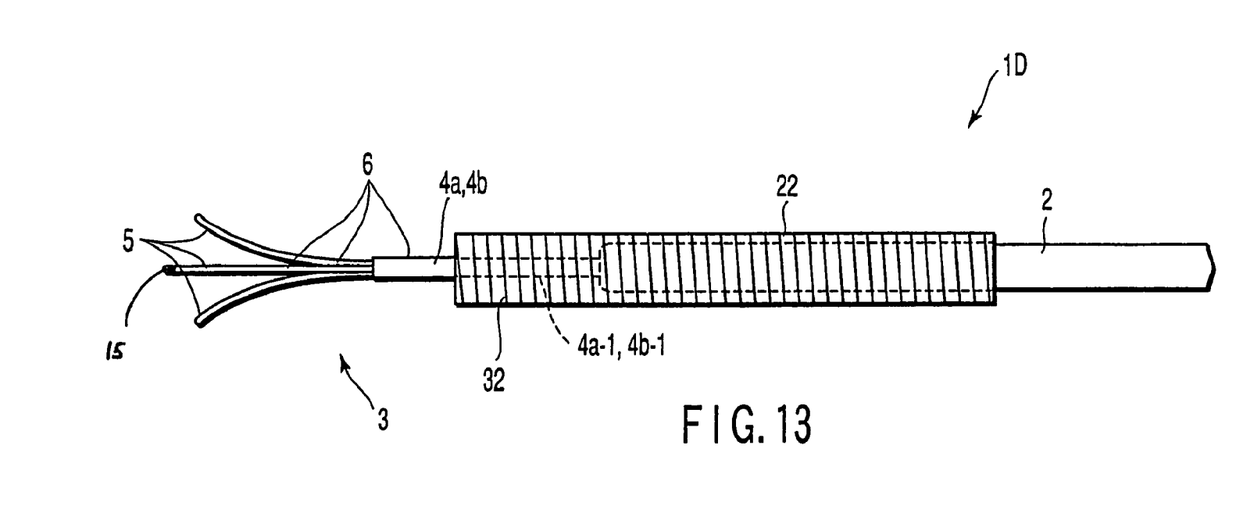
FIG. 13 is a side view of the intravascular obstruction removing wire shown in FIG. 12.

As shown in FIGS. 11 and 13, a trapping portion 3 in an intravascular obstruction removing wire 1D according to this embodiment is formed of a plurality of (three in this embodiment) loop wires 6, in the same manner as in the third embodiment. With the loop wires 6, non-branched wire portions 4a and 4b are formed by twisting the proximal end portions of the loop wires, having a predetermined length s as shown in FIG. 12. More specifically, the proximal end portions on one side of the plurality of loop wires 6 are twisted integrally to form one wire portion 4a, while the proximal ends on the other side are thereof twisted integrally to form the other wire portion 4b. Each of wire portions 4a, 4b has a length s as shown in FIG. 12.

Of three filament portions 5, one located at the center is located on almost the same plane as the non-branched wire portions 4a and 4b, that is, this filament portion is not turned upwardly or downwardly against a plane of FIG. 12. The filament portions 5 on the two sides are turned outwardly with respect to the plane where the non-branched wire portions 4a and 4b extend, as clearly shown in FIGS. 11 and 13. Hence, the intervals between the filament portions 5 at the two sides and the filament portion 5 located at the center increase toward the distal ends of the filament portions 5.

Attaching portions 4a-1 and 4b-1 extending backward from the proximal ends (proximal end-side portions) of the non-branched wire portions 4a and 4b are maintained to be parallel to each other. A first coil 32 is wound on the attaching portions 4a-1 and 4b-1 so as to cover them while binding them. The coil 32 is made of a radiopaque material that does not transmit X-rays. Hence, the position of the trapping portion 3 can be confirmed under X-ray fluoroscopy.

The attaching portions 4a-1 and 4b-1 have outer surfaces integrally covered with the coil 32. The attaching portions 4a-1 and 4b-1 are attached to the distal end of a wire body 2 with a second coil 22 in an aligned state. The coil 22 is wound to cover the coil 32 and the distal end of the wire body 2, and thus extends the distal end of the wire body 2. More specifically, the attaching portions 4a-1 and 4b-1 and the two coils 22 and 23 form the distal end of the wire body 2. The wire portions 4a and 4b extend from this distal end of the wire body 2. The proximal end of the coil 32 is fixed to the distal end of the coil 22 by, e.g., welding by means of brazing or the like, adhesion with an adhesive, or the like. The proximal end of the coil 32 is fixed to the wire body 2 by, e.g., welding by means of brazing, adhesion with an adhesive, or the like.

The outer surfaces of the coils 32 and 22 are smooth so they do not damage a blood vessel wall, thus providing a high safety. The coils 32 and 22 also have, e.g., a function of improving the operability of the wire body 2 in a catheter 8 by decreasing a sliding resistance.

The diameters of the coils 32 and 22 (the thickness of the tapes or flat strands, if the coils are made from the tapes or flat strands) are not particularly limited, but are preferably 0.3 mm to 0.6 mm, and are more preferably 0.4 mm to 0.5 mm.

The materials to form the coils 32 and 22 are not particularly limited, but are preferably various types of metal materials. For example, the coil 32 can be a platinum coil, and the coil 22 can be a stainless steel coil. Then, an effect of improving the visibility under X-ray fluoroscopy can be obtained. The coils 22 and 32 need not be separate members, but can form one coil. In this case, a portion of the coil located at the front portion and a portion thereof located at the rear portion may be made of different materials. For example, the front portion may be made of platinum, while the rear portion may be made of stainless steel, thereby providing an X-ray fluoroscopy effect.

In the fourth embodiment as well, (the proximal ends of) the plurality of loop wires 6 are arranged in a parallel manner (to be substantially parallel to each other), in the same manner as in the third embodiment. As the proximal ends (non-branched wire portions 4a and 4b) of the respective loop wires 6 are retracted into the opening of the catheter 8, they are inwardly displaced, gradually to narrow the interval between them or to small the opening defined by each loop wire. Hence, forces that fasten an embolus 200 act on the outer surface of the embolus, so the embolus 200 can be trapped (held) more reliably.

It can be understood that, in the fourth embodiment, the number, material, turned state, and the like of the loop wires 6 may be equal to those of the third embodiment.

In the fourth embodiment, when compared to the third embodiment, the plurality of loop wires 6 that form the non-branched wire portions 4a and 4b do not come apart from each other because of this arrangement. Therefore, the shape of the trapping portion 3 in the large-diameter state can be maintained more accurately, and the embolus 200 can be held more reliably.

In all the above embodiments, all the filament portions need not be made of the same material, and need not have the same diameter. For example, one of all the filament portions may be made of a radiopaque material. Then, the range of a space where an embolus in the living body is to be trapped can be recognized by means of an X-ray contrast medium. Alternatively, a radiopaque marker 15 may be formed at the distal end of a filament portion. In this case, the radiopaque marker is preferably formed at the distal end of a filament portion which is the most distal end of the trapping portion 3. In the third and fourth embodiments, the radiopaque marker 15 is preferably formed at the distal end of the filament at the center. Such a radiopaque marker can be formed by any means, e.g., by adhesion or winding to the filament portion. For example, the distal end of the filament portion may be formed to have a small diameter, and a marker may be wound on it so the resultant distal end has the same diameter as those of other portions. When a thin platinum wire as a radiopaque marker is wound on a filament portion, preferably a filament portion at the center, a radiopaque marker can be provided to the trapping portion 3. Such a marker can be formed at, e.g., the distal end, of the trapping portion in either the first or second embodiment.

Figure 14A:
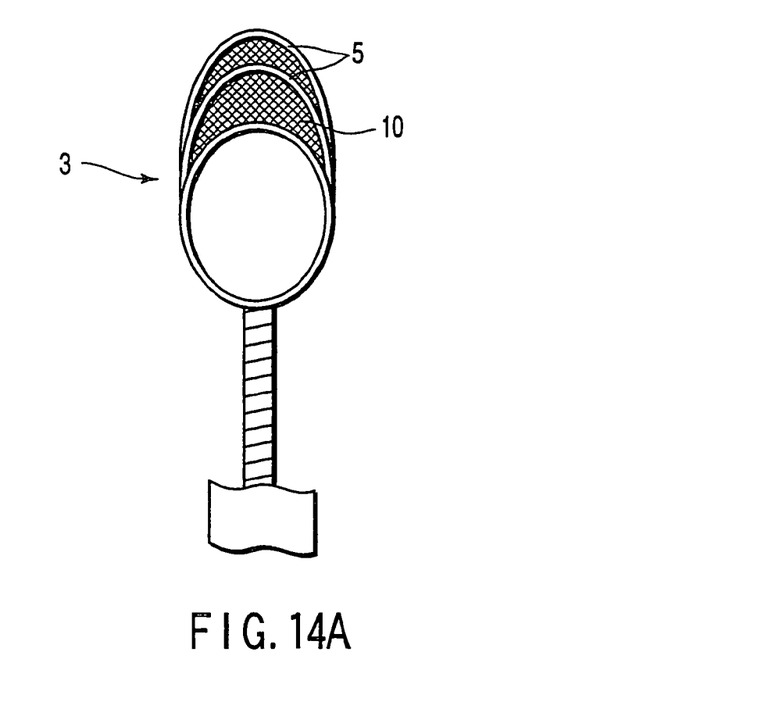
FIGS. 14A and 14B are plan and side views, respectively, for explaining a net applicable to the respective embodiments of the present invention.
Figure 14B:
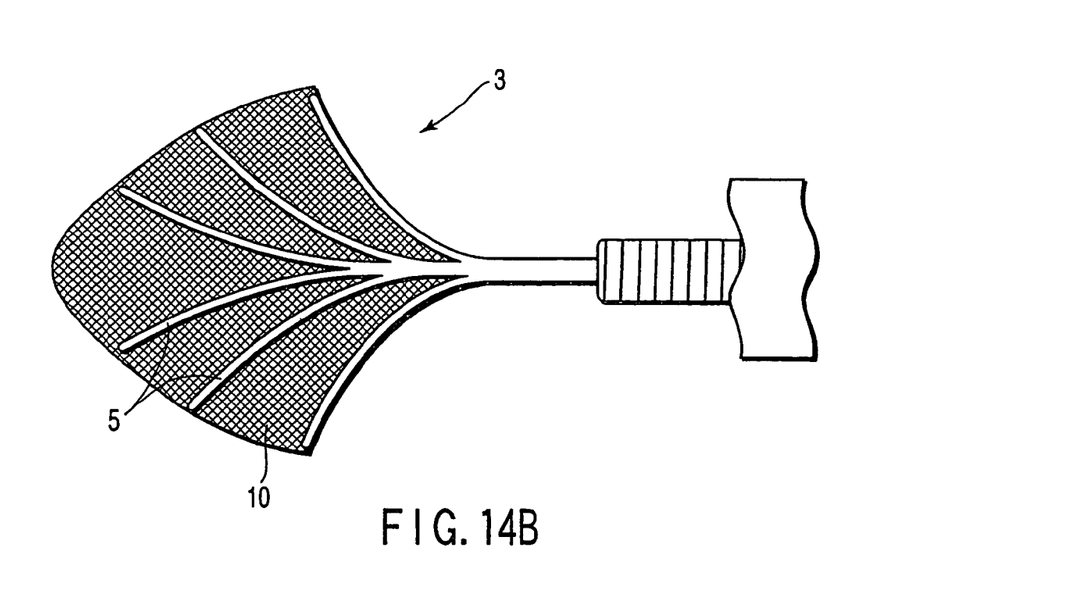

A case wherein a net is applied to the third embodiment will be described with reference to FIGS. 14A and 14B. An example of a net that can be applied to any of all the embodiments described above will be described.

A net 10 is applied to cover the distal end face of a trapping portion 3, i.e., the front surface of a recess where an embolus is to be accommodated. More specifically, the net 10 is applied over filament portions 5 entirely, or between the distal ends of the filament portions 5. The mesh size of the net 10 is selected such that the net 10 passes blood through it but does not pass fractions of an embolus through it.

The net is formed on the front surface of the trapping portion 3. When moving the trapping portion 3 in a blood vessel in order to remove an embolus, even if the embolus in the trapping portion 3 is broken, its fractions can be prevented from escaping from the trapping portion 3.

The intravascular obstruction removing wire and medical instrument according to the present invention have been described by way of the embodiments shown in the drawing, but the present invention is not limited to them. The respective portions that form the intravascular obstruction removing wire and medical instrument can be replaced with those with arbitrary arrangements that can exhibit the same functions.

For example, in the embodiments, the obstruction removing wire has two non-branched wire portions. These wire portions may be three or more branches branching from the distal end of the wire body.

The positions of the non-branched wire portions and filament portions are not limited to those shown in the drawing. For example, at least two filament portions may be arranged to intersect each other.

As has been described above, according to the present invention, an embolus in the blood vessel can be reliably trapped and removed with a simple structure.

The obstruction removing wires of the above embodiments are advantageous in diameter reduction in the small-diameter state, and can be applied to a thin blood vessel as well. Assume an arrangement in which, when the wire body is drawn toward the proximal end with respect to the catheter, the non-branched wire portions come into contact with the distal end opening of the catheter lumen so that the intervals among the wires are narrowed. In this case, the trapping portion can fasten the embolus. Thus, the embolus can be broken or can be held more reliably.

From the above description, the present invention can particularly collect a thrombus that cannot be dissolved by a thrombolytic agent within a short period of time, and is accordingly useful.

The present invention can also be used to treat ischemic diseases (venous embolism, arterial embolism) for which a thrombolytic agent does not work successfully. When the shape and size of the trapping portion are appropriately selected, the present invention is effective for removing an embolus in various types of blood vessels.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An intravascular obstruction removing wire comprising:
an elongate wire body with a distal end;
at least two non-branched wire portions having distal ends and proximal ends, the proximal ends of the non-branched wire portions being connected to the distal end of said elongate wire body, the two non-branched wire portions lying in a plane;
a plurality of non-branched filament portions extending across said non-branched wire portions;
each of said non-branched filament portions having a first end portion, a second end portion, and a loop section extending between the first and second end portions;
the first end portions of all of the non-branched filament portions are gathered at the distal end of one of the non-branched wire portions and connected thereto and the second end portions of all of the non-branched filament portions are gathered at the distal end of another one of the non-branched wire portions and connected thereto so that the intravascular obstruction removing wire has no filament portion which is not gathered at the respective distal ends of the non-branched wire portions, and the loop sections of the non-branched filament portions are separated from each other to form a trapping portion;
said trapping portion is deformable from a large-diameter state in which said non-branched wire portions branch from the distal end of said elongate wire body forward in different directions and said non-branched filament portions are separated from each other, so that a space surrounded by said non-branched wire portions and said non-branched filament portions is formed to trap therein an obstruction in a blood vessel, to a small-diameter state in which said non-branched wire portions are positioned so that a distance between the non-branched wire portions is smaller than that of the non-branched wire portions in the large-diameter state; and
the plurality of non-branched filament portions comprising a first filament portion, a second filament portion and a third filament portion, the loop section of the first filament portion being positioned entirely on one side of the plane, the loop section of the second filament portion being positioned entirely on the opposite side of the plane, the loop section of the third filament portion lying approximately in the plane.

2. A wire according to claim 1, wherein said non-branched wire portions and said non-branched filament portions have an elastic property, and said trapping portion is deformable from the small-diameter state to the large-diameter state by an elastic restoring force thereof.

3. A wire according to claim 1, wherein said trapping portion has a radiopaque marker portion.

4. The intravascular obstruction removing wire of claim 1, wherein the loop section of each non-branched filament portion is formed only of a wire.

5. A wire according to claim 2, wherein the distal ends of said non-branched wire portions are separate from each other, and the loop sections of the non-branched filament portions define projecting portions separate from each other in directions away from the plane on which said non-branched wire portions extend.

6. A wire according to claim 5, wherein a distance between adjacent ones of the projecting portions of said plurality of non-branched filament portions increases toward their distal ends.

7. A wire according to claim 6, wherein the adjacent projecting portions are extended from the end portions at different angles with respect to the plane.

8. A wire according to claim 6, wherein the projecting portion of at least one of said plurality of non-branched filament portions, which is the farthest from the plane, has a curved portion which is turned such that a central portion thereof is further separate from the plane.

9. A wire according to claim 6, wherein the projecting portions of said non-branched filament portions are curved to project forward.

10. A wire according to claim 6, wherein said non-branched filament portions comprise loop wires, said first and second end portions define a pair of proximal end portions and said loop section defines a loop portion extending from the proximal end portions, and the proximal end portions of the plurality of loop wires being gathered integrally to form said non-branched wire portions.

11. A wire according to claim 10, wherein the proximal end portions of the loop wires are in tight contact with each other to form said non-branched wire portions.

12. A wire according to claim 11, wherein the plurality of loop wires have the same length.

13. A wire according to claim 11, wherein the proximal end portions of the loop wires are twisted integrally to form said non-branched wire portions.

14. A wire according to claim 13, wherein said non-branched wire portions have attaching portions integrally extending therefrom, and
further comprising a first member for integrally fixing the attaching portions to each other, and a second member for connecting said first member to said wire body so as to form the distal end of said wire body.

15. A wire according to claim 14, wherein the first member has a first coil wound in common around the two attaching portions, and the second member has a second coil wound in common around the first coil and part of said wire body.

16. A medical instrument comprising:
   a catheter having a lumen and a distal end face to be positioned in a blood vessel; and
   an obstruction removing wire inserted in the lumen and inserted in the blood vessel from the distal end face,
   said obstruction removing wire comprising
      an elongate wire body with a distal end,
      at least two non-branched wire portions having distal ends and proximal ends, the proximal ends of the non-branched wire portions being connected to the distal end of said elongate wire body, the two non-branched wire portions lying in a plane;
      a plurality of non-branched filament portions extending across said non-branched wire portions,
      each of said non-branched filament portions having a first end portion, a second end portion, and a loop section extending between the first and second end portions;
      the first end portions of all of the non-branched filament portions are gathered at the distal end of one of the non-branched wire portions and connected thereto and the second end portions of all of the non-branched filament portions are gathered at the distal end of another one of the non-branched wire portions and connected thereto so that the intravascular obstruction removing wire has no filament portion which is not gathered at the respective distal ends of the non-branched wire portions, and the loop sections of the non-branched filament portions are separated from each other to form a trapping portion;
   said trapping portion is deformable from a large-diameter state in which said non-branched wire portions branch from the distal end of said elongate wire body forward in different directions and said non-branched filament portions are separated from each other, so that a space surrounded by said non-branched wire portions and said non-branched filament portions is formed to trap therein an obstruction in a blood vessel, to a small-diameter state in which said non-branched wire portions are positioned so that a distance between the non-branched wire portions is smaller than that of the non-branched wire portions in the large-diameter state; and
   the plurality of non-branched filament portions comprising a first filament portion, a second filament portion and a third filament portion, the loop section of the first filament portion being positioned entirely on one side of the plane, the loop section of the second filament portion being positioned entirely on the opposite side of the plane, the loop section of the third filament portion lying approximately in the plane.

17. An instrument according to claim 16, wherein said non-branched filament portions are deformed to reduce the space as said trapping portions enters the lumen from the front end face of said catheter, thereby sandwiching the obstruction trapped in the space together with the front end face of said catheter.

18. The medical instrument of claim 16, wherein the loop section of each non-branched filament portion is formed only of a wire.

19. An intravascular obstruction removing wire comprising:
   an elongate wire body with a distal end;
   at least two non-branched wire portions having distal ends and proximal ends, the proximal ends of the non-branched wire portions being connected to the distal end of said elongate wire body, the two non-branched wire portions lying in a plane;
   a plurality of filament portions extending across said non-branched wire portions, each of the filament portions being formed of a non-branched wire so that a continuous space is formed between the adjacent filament portions;
   each of said filament portions having a first end portion, a second end portion, and a loop section extending between the first and second end portion;
   the first end portions of the plurality of filament portions are gathered at the distal end of one of the non-branched wire portions and connected thereto and the second end portions of the plurality of filament portions are gathered at the distal end of another one of the non-branched wire portions and connected thereto, and the loop sections of the filament portions are separated from each other to form a trapping portion;
   said trapping portion is deformable from a large-diameter state in which said non-branched portions branch from the distal end of said wire body forward in different directions and said filament portions are separated from each other, so that a space surrounded by said non-branched wire portions and said filament portions is formed to trap therein an obstruction in a blood vessel, to a small-diameter state in which said non-branched wire portions are positioned so that a distance between the non-branched wire portions is smaller than that of the non-branched wire portions in the large-diameter state; and
   the plurality of non-branched filament portions comprising a first filament portion, a second filament portion and a third filament portion, the loop section of the first filament portion being positioned entirely on one side of the plane, the loop section of the second filament portion being positioned entirely on the opposite side of the plane, the loop section of the third filament portion lying approximately in the plane.

20. The intravascular obstruction removing wire of claim 19, wherein each filament portion is formed only of a wire.

21. An intravascular obstruction removing wire comprising:
   an elongate wire body with a distal end;
   at least two non-branched wire portions having distal ends and proximal ends, the proximal ends of the non-branched wire portions being connected to the distal end of said elongate wire body, the two non-branched wire portions lying in a plane;
   a plurality of non-branched filament portions extending across said non-branched wire portions;
   each of said non-branched filament portions has a first end portion, a second end portion, and a loop section extending between the first and second end portions thereof;
   the first end portions of the plurality of non-branched filament portions are gathered at the distal end of one of the non-branched wire portions and connected thereto and the second end portions of the plurality of non-branched filament portions are gathered at the distal end of another one of the non-branched wire portions and connected thereto, and the loop sections of the filament portions are separated from each other to form a trapping portion;
   said non-branched filament portions comprising loop wires, said first and second end portions defining a pair of proximal end portions and said loop section defining a loop portion extending from the proximal end portions, and the proximal end portions of the plurality of loop wires being gathered integrally to form said non-branched wire portions;

said trapping portion is deformable from a large-diameter state in which said non-branched wire portions branch from the distal end of said elongate wire body forward in different directions and said non-branched filament portions are separated from each other, so that a space surrounded by said non-branched wire portions and said non-branched filament portions is formed to trap therein an obstruction in a blood vessel, to a small-diameter state in which said non-branched wire portions are positioned so that a distance between the non-branched wire portions is smaller than that of the non-branched wire portions in the large-diameter state; and the plurality of non-branched filament portions comprising a first filament portion, a second filament portion and a third filament portion, the loop section of the first filament portion being positioned entirely on one side of the plane, the loop section of the second filament portion being positioned entirely on the opposite side of the plane, the loop section of the third filament portion lying approximately in the plane.

22. A wire according to claim 21, wherein the proximal end portions gathered in each of the non-branched wire portions are arranged substantially in a linear line normal to the plane on which said non-branched wire portions extend.

23. The intravascular obstruction removing wire of claim 21, wherein the loop sections of each non-branched filament portion is formed only of a wire.

24. An intravascular obstruction removing wire comprising:

an elongate wire body with a distal end;

at least two non-branched wire portions having distal ends and proximal ends which are connected to the distal end of said elongate wire main body, the two non-branched wire portions lying in a plane;

a plurality of non-branched filament portions extending across said non-branched wire portions, each of said plurality of non-branched filament portions has a first end portion and a second end portion, the first end portions of the plurality of non-branched filament portions are gathered at the distal end of one of the non-branched wire portions and connected thereto, and the second end portions of the plurality of non-branched filament portions are gathered at the distal end of another one of the non-branched wire portions and connected thereto;

wherein said non-branched wire portions and said non-branched filament portions form a trapping portion;

said trapping portion is deformable from a large-diameter state in which said non-branched portions branch from the distal end of said elongate wire body forward in different directions and said non-branched filament portions are separated from each other, so that a space surrounded by said non-branched wire portions and said non-branched filament portions is formed to trap therein an obstruction in a blood vessel, to a small-diameter state in which said non-branched wire portions are positioned so that a distance between the non-branched wire portions is smaller than that of the non-branched wire portions in the large-diameter state;

the plurality of non-branched filament portions comprising a first filament portion, a second filament portion and a third filament portion, the loop section of the first filament portion being positioned entirely on one side of the plane, the loop section of the second filament portion being positioned entirely on the opposite side of the plane; and the third filament portion being located on approximately the same plane as the plane on which the non-branched wire portions are located, and being provided with a radiopaque marker.

25. A wire according to claim 24, wherein said wire comprises, in total, an odd number of non-branched filament portions.

26. The intravascular obstruction removing wire of claim 24, wherein an elongate wire is not present on a distal end side of the trapping portion.

* * * * *